(12) United States Patent  
Marvel

(10) Patent No.: US 7,976,578 B2
(45) Date of Patent: Jul. 12, 2011

(54) BUFFER FOR A HUMAN JOINT AND METHOD OF ARTHROSCOPICALLY INSERTING

(76) Inventor: James Marvel, Mineola, TX (US)

( * ) Notice: Subject to any disclaimer, the term of this patent is extended or adjusted under 35 U.S.C. 154(b) by 255 days.

(21) Appl. No.: 12/133,211

(22) Filed: Jun. 4, 2008

(65) Prior Publication Data

US 2009/0306778 A1 Dec. 10, 2009

(51) Int. Cl.
*A61F 2/08* (2006.01)
(52) U.S. Cl. .................................................. 623/14.12
(58) Field of Classification Search .... 623/17.11–17.16, 623/14.12, 16.11, 18.11, 19.11, 20.11, 20.14, 623/20.15, 20.16
See application file for complete search history.

(56) References Cited

U.S. PATENT DOCUMENTS

| | | | | | |
|---|---|---|---|---|---|
| 4,344,193 | A | * | 8/1982 | Kenny | 623/14.12 |
| 4,502,161 | A | | 3/1985 | Wall | |
| 4,502,161 | A | | 7/1989 | Wall | |
| 4,863,477 | A | * | 9/1989 | Monson | 623/17.12 |
| 4,880,429 | A | * | 11/1989 | Stone | 623/14.12 |
| 4,919,667 | A | * | 4/1990 | Richmond | 623/14.12 |
| 4,932,969 | A | * | 6/1990 | Frey et al. | 623/17.12 |
| 5,092,894 | A | * | 3/1992 | Kenny | 128/898 |
| 5,158,574 | A | | 10/1992 | Stone | |
| 5,171,281 | A | * | 12/1992 | Parsons et al. | 623/17.15 |
| 5,344,459 | A | * | 9/1994 | Swartz | 623/14.12 |
| 5,545,229 | A | * | 8/1996 | Parsons et al. | 623/17.15 |
| 5,549,679 | A | * | 8/1996 | Kuslich | 623/17.12 |
| 5,571,189 | A | * | 11/1996 | Kuslich | 623/17.12 |
| 5,645,597 | A | * | 7/1997 | Krapiva | 606/279 |
| 5,800,549 | A | * | 9/1998 | Bao et al. | 606/99 |
| 5,824,093 | A | * | 10/1998 | Ray et al. | 623/17.16 |
| 6,022,376 | A | * | 2/2000 | Assell et al. | 623/17.16 |
| 6,046,379 | A | * | 4/2000 | Stone et al. | 623/14.12 |
| 6,132,465 | A | * | 10/2000 | Ray et al. | 623/17.16 |
| 6,395,032 | B1 | * | 5/2002 | Gauchet | 623/17.12 |

(Continued)

FOREIGN PATENT DOCUMENTS

WO WO 02/39889 A2 5/2002

(Continued)

OTHER PUBLICATIONS

Communication pursuant to Article 94(3) EPC dated Aug. 1, 2010, issued by the European Patent Office in European Patent Application No. 09007304.0; Applicant: Marvel, James.

(Continued)

*Primary Examiner* — Alvin J. Stewart
(74) *Attorney, Agent, or Firm* — Hovey Williams LLP

(57) ABSTRACT

A buffer (10) for placement in a human knee between the femur and tibia comprises an outer sack (14) formed of a pliable material and having a one-way valve (22), a generally circularly shaped inner ring (16) received within the outer sack (14), and a friction reducing fluid (18) received within the outer sack (14) via the one-way valve (22). The inner ring (16) includes top and bottom surfaces (38,40) angled inwardly with respect to each other, such that the ring (16) is generally concave. The buffer (10) is configured for insertion between the femur and tibia so as to at least partially prevent the bones from contacting each other, which reduces the pain and discomfort associated with a loss of articular cartilage (12). The buffer (10) is arthroscopically inserted in the knee using an especially designed sleeve (20) configured for support of the buffer (10) during insertion.

15 Claims, 3 Drawing Sheets

U.S. PATENT DOCUMENTS

| | | | | |
|---|---|---|---|---|
| 6,419,704 B1* | 7/2002 | Ferree | | 623/17.12 |
| 6,425,920 B1* | 7/2002 | Hamada | | 623/17.16 |
| 6,436,146 B1* | 8/2002 | Hassler et al. | | 623/21.11 |
| 6,482,234 B1* | 11/2002 | Weber et al. | | 623/17.12 |
| 6,527,804 B1* | 3/2003 | Gauchet et al. | | 623/17.12 |
| 6,582,466 B1* | 6/2003 | Gauchet | | 623/17.11 |
| 6,679,914 B1* | 1/2004 | Gabbay | | 623/14.12 |
| 6,712,853 B2* | 3/2004 | Kuslich | | 623/17.16 |
| 6,733,533 B1* | 5/2004 | Lozier | | 623/17.12 |
| 6,923,831 B2* | 8/2005 | Fell et al. | | 623/14.12 |
| 6,969,404 B2* | 11/2005 | Ferree | | 623/17.11 |
| 6,994,730 B2 | 2/2006 | Posner | | |
| 7,001,385 B2* | 2/2006 | Bonutti | | 606/60 |
| 7,004,971 B2* | 2/2006 | Serhan et al. | | 623/17.16 |
| 7,077,865 B2* | 7/2006 | Bao et al. | | 623/17.12 |
| 7,244,273 B2* | 7/2007 | Pedersen et al. | | 623/14.12 |
| 7,250,060 B2* | 7/2007 | Trieu | | 623/17.15 |
| 7,252,685 B2* | 8/2007 | Bindseil et al. | | 623/16.11 |
| 7,291,169 B2* | 11/2007 | Hodorek | | 623/14.12 |
| 7,297,161 B2* | 11/2007 | Fell | | 623/14.12 |
| 7,476,250 B1* | 1/2009 | Mansmann | | 623/14.12 |
| 7,485,145 B2* | 2/2009 | Purcell | | 623/17.12 |
| 7,491,235 B2* | 2/2009 | Fell | | 623/14.12 |
| 7,611,653 B1* | 11/2009 | Elsner et al. | | 264/255 |
| 7,618,457 B2* | 11/2009 | Hudgins | | 623/17.12 |
| 7,618,461 B2* | 11/2009 | Trieu | | 623/17.16 |
| 7,641,691 B2* | 1/2010 | Lotz et al. | | 623/17.12 |
| 7,645,301 B2* | 1/2010 | Hudgins et al. | | 623/17.12 |
| 7,713,301 B2* | 5/2010 | Bao et al. | | 623/17.12 |
| 7,713,303 B2* | 5/2010 | Trieu et al. | | 623/17.16 |
| 7,717,956 B2* | 5/2010 | Lang | | 623/14.12 |
| 7,744,630 B2* | 6/2010 | Lancial | | 606/247 |
| 7,771,476 B2* | 8/2010 | Justis et al. | | 623/17.11 |
| 7,883,527 B2* | 2/2011 | Matsuura et al. | | 606/213 |
| 2002/0035400 A1* | 3/2002 | Bryan et al. | | 623/17.15 |
| 2002/0147496 A1* | 10/2002 | Belef et al. | | 623/17.12 |
| 2002/0147497 A1* | 10/2002 | Belef et al. | | 623/17.12 |
| 2002/0183848 A1* | 12/2002 | Ray et al. | | 623/17.12 |
| 2003/0009224 A1* | 1/2003 | Kuras | | 623/17.16 |
| 2003/0093152 A1* | 5/2003 | Pedersen et al. | | 623/14.12 |
| 2003/0195628 A1* | 10/2003 | Bao et al. | | 623/17.12 |
| 2004/0148026 A1* | 7/2004 | Bonutti | | 623/16.11 |
| 2004/0193273 A1* | 9/2004 | Huang | | 623/17.12 |
| 2004/0215342 A1* | 10/2004 | Suddaby | | 623/17.12 |
| 2004/0243250 A1* | 12/2004 | Stone et al. | | 623/23.72 |
| 2005/0049604 A1* | 3/2005 | Singer et al. | | 606/90 |
| 2005/0090901 A1* | 4/2005 | Studer | | 623/17.12 |
| 2005/0113923 A1* | 5/2005 | Acker et al. | | 623/17.12 |
| 2005/0177240 A1* | 8/2005 | Blain | | 623/17.15 |
| 2005/0197702 A1* | 9/2005 | Coppes et al. | | 623/17.12 |
| 2005/0234549 A1* | 10/2005 | Kladakis et al. | | 623/14.12 |
| 2005/0251259 A1* | 11/2005 | Suddaby | | 623/17.12 |
| 2005/0267580 A1* | 12/2005 | Suddaby | | 623/17.12 |
| 2006/0047341 A1* | 3/2006 | Trieu | | 623/17.16 |
| 2006/0052874 A1* | 3/2006 | Johnson et al. | | 623/17.16 |
| 2006/0149370 A1 | 7/2006 | Schmieding et al. | | |
| 2006/0241758 A1* | 10/2006 | Peterman et al. | | 623/17.11 |
| 2006/0241765 A1* | 10/2006 | Burn et al. | | 623/17.12 |
| 2006/0241766 A1* | 10/2006 | Felton et al. | | 623/17.12 |
| 2006/0247780 A1* | 11/2006 | Bert | | 623/17.16 |
| 2006/0293751 A1* | 12/2006 | Lotz et al. | | 623/17.12 |
| 2007/0027547 A1* | 2/2007 | Rydell et al. | | 623/21.18 |
| 2007/0050032 A1* | 3/2007 | Gittings et al. | | 623/17.12 |
| 2007/0050033 A1* | 3/2007 | Reo et al. | | 623/17.12 |
| 2007/0100450 A1* | 5/2007 | Hodorek | | 623/14.12 |
| 2007/0118218 A1* | 5/2007 | Hooper | | 623/14.12 |
| 2007/0168031 A1* | 7/2007 | Hudgins et al. | | 623/17.12 |
| 2007/0168042 A1* | 7/2007 | Hudgins et al. | | 623/17.16 |
| 2007/0173940 A1* | 7/2007 | Hestad et al. | | 623/17.12 |
| 2007/0179606 A1* | 8/2007 | Huyghe et al. | | 623/14.12 |
| 2007/0233258 A1* | 10/2007 | Hestad et al. | | 623/17.12 |
| 2007/0250060 A1* | 10/2007 | Anderson et al. | | 606/61 |
| 2007/0293947 A1* | 12/2007 | Mansmann | | 623/14.12 |
| 2008/0015703 A1* | 1/2008 | Casey | | 623/17.16 |
| 2008/0046082 A1* | 2/2008 | Lee | | 623/17.16 |
| 2008/0051889 A1* | 2/2008 | Hodorek | | 623/14.12 |
| 2008/0051896 A1* | 2/2008 | Suddaby | | 623/17.12 |
| 2008/0071374 A1* | 3/2008 | Steinberg | | 623/17.12 |
| 2008/0086133 A1* | 4/2008 | Kuslich et al. | | 606/61 |
| 2008/0086210 A1* | 4/2008 | Fox | | 623/14.12 |
| 2008/0132934 A1* | 6/2008 | Reiley et al. | | 606/192 |
| 2008/0154371 A1* | 6/2008 | Fell et al. | | 623/14.12 |
| 2008/0195210 A1* | 8/2008 | Milijasevic et al. | | 623/17.16 |
| 2008/0208341 A1* | 8/2008 | McCormack et al. | | 623/17.12 |
| 2008/0243249 A1* | 10/2008 | Kohm et al. | | 623/17.12 |
| 2008/0300687 A1* | 12/2008 | Lin et al. | | 623/17.12 |
| 2009/0012615 A1* | 1/2009 | Fell | | 623/14.12 |
| 2009/0024219 A1* | 1/2009 | McLeer | | 623/17.16 |
| 2009/0030399 A1* | 1/2009 | Raiszadeh | | 604/506 |
| 2009/0036926 A1* | 2/2009 | Hestad | | 606/247 |
| 2009/0076605 A1* | 3/2009 | Linares | | 623/14.12 |
| 2009/0082870 A1* | 3/2009 | Osman | | 623/17.16 |
| 2009/0112221 A1* | 4/2009 | Burke et al. | | 606/102 |
| 2009/0112323 A1* | 4/2009 | Hestad et al. | | 623/17.12 |
| 2009/0118833 A1* | 5/2009 | Hudgins et al. | | 623/17.16 |
| 2009/0125108 A1* | 5/2009 | Linares | | 623/14.12 |
| 2009/0157119 A1* | 6/2009 | Hale | | 606/247 |
| 2009/0182377 A1* | 7/2009 | Petersen | | 606/247 |
| 2009/0222093 A1* | 9/2009 | Liu et al. | | 623/17.12 |
| 2009/0226068 A1* | 9/2009 | Fitz et al. | | 382/131 |
| 2009/0259314 A1* | 10/2009 | Linder-Ganz et al. | | 623/14.12 |
| 2009/0276045 A1* | 11/2009 | Lang | | 623/14.12 |
| 2009/0299476 A1* | 12/2009 | Diwan et al. | | 623/17.12 |
| 2010/0023126 A1* | 1/2010 | Grotz | | 623/14.12 |
| 2010/0070032 A1* | 3/2010 | Park | | 623/17.12 |
| 2010/0168859 A1* | 7/2010 | Wardlaw | | 623/17.12 |
| 2010/0204794 A1* | 8/2010 | Jarzem et al. | | 623/17.12 |
| 2010/0228257 A1* | 9/2010 | Bonutti | | 606/87 |
| 2010/0262240 A1* | 10/2010 | Chavatte et al. | | 623/17.11 |
| 2010/0268343 A1* | 10/2010 | Dewey et al. | | 623/17.16 |
| 2010/0280615 A1* | 11/2010 | Baumgartner et al. | | 623/17.12 |
| 2010/0292798 A1* | 11/2010 | Maestretti | | 623/17.12 |
| 2010/0318190 A1* | 12/2010 | Collins et al. | | 623/17.12 |
| 2011/0004308 A1* | 1/2011 | Marino et al. | | 623/17.12 |
| 2011/0022089 A1* | 1/2011 | Assell et al. | | 606/247 |

FOREIGN PATENT DOCUMENTS

WO  WO 2006/097932 A2  9/2006

OTHER PUBLICATIONS

Knee Joint—Anatomy & Function, Apr. 3, 2003, The Center for Orthopaedics and Sports Medicine, Marietta, GA, Copyrighted 1999.

Knee Arthroscopy, Apr. 3, 2003, The Center for Orthopaedics and Sports Medicine, Marietta, GA, Copyrighted 1999.

Meniscal Repair, Apr. 3, 2003, The Center for Orthopaedics and Sports Medicine, Marietta, GA, Copyrighted 1999.

Meniscal Tear, Aug. 2007, American Academy of Orthopaedic Surgeons, Rosemont, IL, Copyrighted 2007.

Knee Arthroscopy, Aug. 2007, American Academy of Orthopaedic Surgeons, Rosemont, IL, Copyrighted 2007.

Cluett, Jonathan, Meniscus Repair, About.com: Orthopedics, Mar. 25, 2007.

Avery, F. Lincoln, M.D., The Meniscus: Shock Absorber for the Knee, Orthopaedic Associates of Portland, Portland, ME, Copyrighted 2007.

Torn Cartilage (Meniscus), Apr. 3, 2003, The Center for Orthopaedics and Sports Medicine, Marietta, GA, Copyrighted 1999.

European Search Report dated Aug. 27, 2009 issued by the European Patent Office in European Patent Application No. 09007304.0; Applicant: Marvel, James.

* cited by examiner

BUFFER FOR A HUMAN JOINT AND METHOD OF ARTHROSCOPICALLY INSERTING

BACKGROUND

1. Field

Embodiments of the present invention relate to apparatus and methods of providing a buffer for a human joint so as to prevent painful bone on bone contact. More particularly, embodiments of the present invention present a buffer for insertion between the femur and tibia in the human knee, so as to protect worn or damaged articular cartilage or exposed bone and to allow the articular surfaces remaining on the femur and tibia to continue to move against each other less painfully.

2. Description of the Related Art

The human knee joint is one of the most complex joints of the body and is also highly susceptible to damage because it is a weight bearing joint. The knee joint itself is comprised of the femur (thigh bone), the tibia (shin bone), the patella (kneecap), articular cartilage, and menisci, which are a type of crescent-shaped cartilage that lies between the femur and tibia. The menisci are located in the medial and lateral articulations of the knee and sometimes act as shock-absorbing pads. The knee is also compromised of tissues that are muscle, ligament, the lining tissue (synovium), and the synovial fluid which is secreted by the synovium.

The ends of the femur and tibia are coated with articular cartilage, which is smooth and hard, so as to provide the femur, tibia, and patella with a slick surface during normal movement. The articular cartilage has a very low coefficient of friction and can also receive large compressive loads, which makes it vital to ensure ease of movement of the knee joint and prevent bone on bone contact between the femur and tibia. Normal articular cartilage is about 50 times slicker than ice.

Over time, the articular cartilage on the femur and tibia, and in any other human joint, wears and degenerates, such that it thins or in some joints is completely lost. Upon wear of the articular cartilage, the slick, low friction surfaces from the cartilage are lost, and the ends of the femur and tibia banes are exposed. Without any protecting articular cartilage, the femur and tibia contact each. This bone on bone contact is painful, and is often the end result of osteoarthritis. Additionally, bones can also become hard and sclerotic over time with associated loss of articular cartilage, which can further increases the pain.

Many methods have been developed to either replace worn cartilage or otherwise minimize the pain associated with the loss of the articular cartilage. The methods have all had varying degrees of success but are often accompanied by very extensive and invasive surgery. All invasive methods are costly, often requiring implanting nonbiologic parts within the knee, or, in some instances, human cadaver parts. These methods of treatment also require lengthy rehabilitation, which often times leaves the patient in considerable pain.

One method of treatment that has been used is implantation of cadaver menisci. This method has had only limited success and multiple failures. A second method is chondroplasty, or removal of and thinning out the existing damaged cartilage. This method is used to smooth the cartilage to reduce the friction between the femur and tibia, and remove the flaps of cartilage that have delaminated from the bone. The success of this procedure is limited by the amount of cartilage remaining, and doctors guard against removal of too much of the articular cartilage so as to prevent exposure of the subchondral bone. For older patients or patients with traumatic arthritis of their knees, chondroplasty has only limited application because of the lack of healthy articular cartilage.

If the articular cartilage loss is small, an osteochondral autograft transplant (known as an OATS procedure) can be performed. The OATS procedure requires removing a dowel shaped portion of bone and replacing it with a commensurate dowel shaped portion of articular cartilage from another area of the knee, another joint, or even a cadaver. The OATS procedure is relatively invasive, has a fairly lengthy rehabilitation time, and has also only had limited success.

An even further alternative to repairing articular cartilage damage is growing the patient's own cartilage in tissue cultures and placing the newly grown cartilage in the areas of cartilage loss. This is an expensive and often unsuccessful method of treatment.

In the most extreme of cases of arthritis, the knee joint may be artificially resurfaced or even replaced. In artificial joint replacement, the ends of the femur and tibia are capped with plastic or metal pieces that are cemented to the ends of the bone. Alternatively, the ends of the femur and tibia can be replaced with a biologic ingrowth coating of the metal used, which removes the need for the cement. This procedure is presently the standard approach to treating severe osteoarthritis of the knee; however, the risks from this procedure are numerous, and this is particularly unfortunate for patients who can ill afford a major complication from this extensive surgery. In places where these artificial joints have been inserted, wear eventually occurs in the polyethylene surface between the metal caps, which can lead to bone destruction just from the particles of the polyethylene. Moreover, this procedure is not only quite invasive but requires a lengthy rehabilitation time. Thus, for these reasons, many doctors delay as long as possible this invasive procedure in many patients.

An even further method of treatment is arthrosporic debridement, which is much less invasive but almost always unsuccessful in limiting the pain from the damaged joint surface, unless most of the pain is from a torn cartilage or loose body in the joint that can be removed arthroscopically.

The problems associated with each of the above procedures are highly dependant on the age and medical condition of the patient. For older patients, their ability and desire to engage in an invasive procedure that requires lengthy rehabilitation is often limited. Moreover, for older patients who are not necessarily engaging in many activities or who do not require a long-term solution to adjust their pain and discomfort, having an invasive, complicated procedure performed is not ideal.

Accordingly, there is a need for a less risky and improved apparatus and method for alleviating and addressing pain resulting from a loss of articular cartilage. There is a need for a new apparatus and method of treatment of lost cartilage that extends beyond attempting to fix or replace damaged cartilage, but instead provides an apparatus and method of treatment that is minimally invasive, relatively inexpensive requires relatively short rehabilitation time, and is suitable for older patients. This invention solves many of the above-described problems and provides a distinct advantage in the art of medical treatment for prevention of bone on bone contact due to the loss of articular cartilage. More particularly this invention provides a new apparatus and method of treatment to address the pain and discomfort associated with the loss of articular cartilage by interposing a thin but slick barrier between the tibia and femur. This invention provides a buffer between the femur and tibia in the human knee that does not require suturing or other permanent securement to muscles, ligaments, or tendons in the knee.

SUMMARY

The present invention solves the above-described problems and provides a distinct advance in the art of medical treatments for prevention of bone-on-bone contact due to the loss of articular cartilage. More particularly, the present invention provides a new method of treatment to address the pain and discomfort associated with the loss of articular cartilage. In particular, embodiments of the present invention provide a buffer independently held between a human's femur and tibia and that does not require suturing or other permanent securement to any muscle, ligament, or tendon in the knee.

The buffer of embodiments of the present invention comprises an outer sack formed of a pliable material and having a one-way valve; a generally circularly-shaped, rigid inner ring within the outer sack, the inner ring having a top surface and a bottom surface angled inwardly with respect to each other, such that the ring is generally concave; and a friction reducing fluid received within the outer sack via the one-way valve.

The buffer is inserted into the knee joint using a specially designed sleeve comprising a body and a stylus or plunger. The body is generally an ovoid hollow tube into which is inserted the buffer. The stylus or plunger includes a fluid line comprising a tube through which a fluid can be pumped. The fluid line and buffer, when received within the sleeve, are in fluid communication, such that the fluid can be inserted into the outer sack of the buffer once the buffer is positioned in the knee joint.

To insert the buffer into the sleeve, the buffer is compressed into the sleeve, and the stylus is screwed or otherwise secured to the rigid inner ring of the buffer. The stylus is then unscrewed from the buffer once the device is positioned in the knee joint and after the fluid is placed into the buffer via a one way valve in the buffer.

A method of inserting the buffer into the knee comprises the steps of providing the buffer, providing a sleeve having a stylus operable to securely receive the buffer during insertion, and injecting fluid into the outer sack during insertion via the one way valve located in the buffer. To insert the buffer in the sleeve, the buffer is compressed side to side, placed into the sleeve, and removably secured to the stylus. After being placed into the knee, the buffer is then injected with fluid to help the surfaces of the buffer move over each other by reducing friction between them. Once the buffer is injected with this fluid, the stylus is unscrewed form the rigid inner ring, the fluid is held in place by the one way valve, the sleeve is removed, the skin is closed, and the operation is complete.

BRIEF DESCRIPTION OF THE DRAWING FIGURES

Embodiments of the present invention are described in detail below with reference to the attached drawing figures, wherein.

Figure 1:
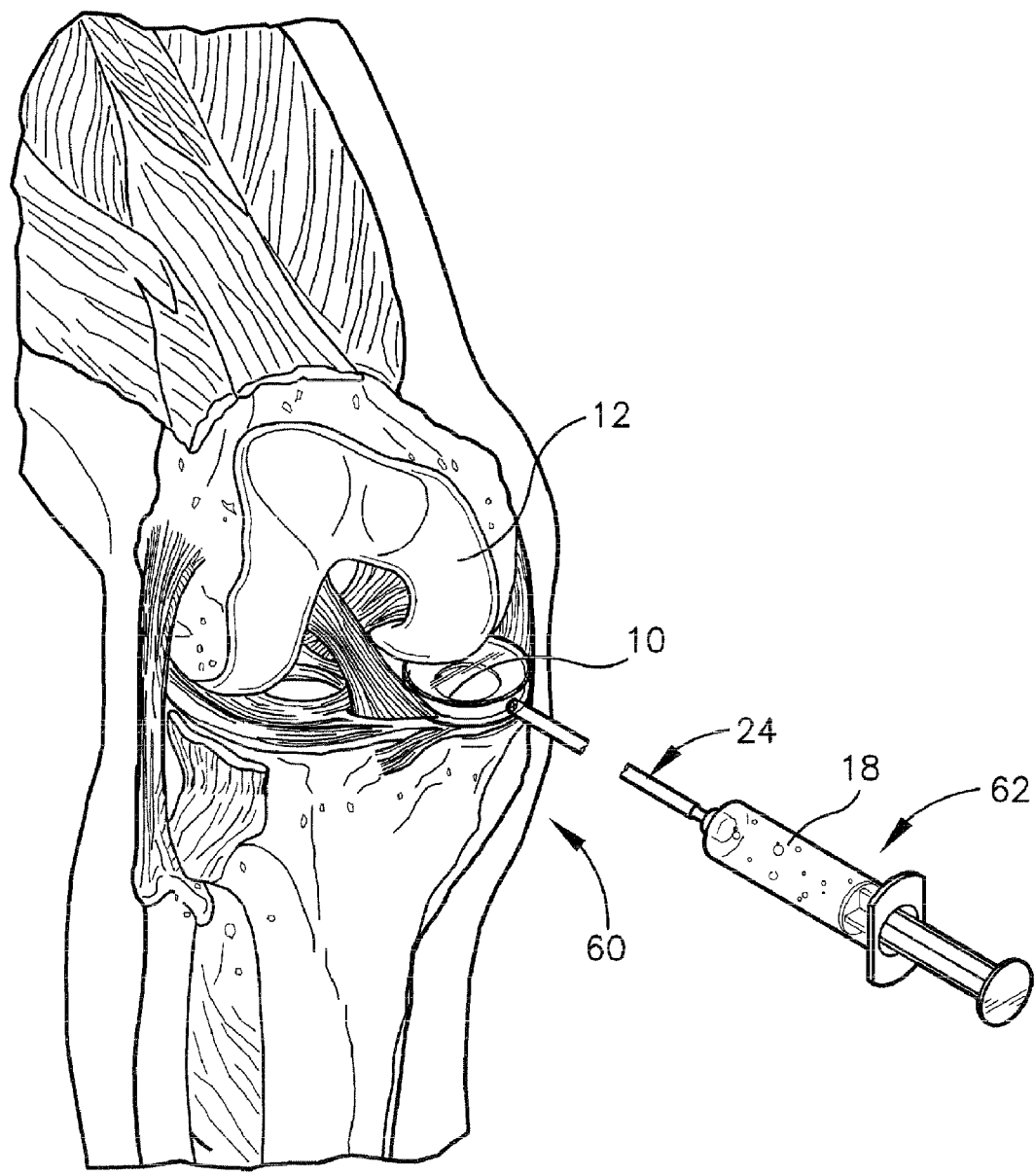
FIG. 1 is a perspective view of a human knee showing the skin removed and illustrating the femur, tibia, articular cartilage covering ends of the femur and tibia, and menisci.

The drawing figures do not limit the present invention to the specific embodiments disclosed and described herein. The drawings are not necessarily to scale, emphasis instead being placed upon clearly illustrating the principles of the invention.

DETAILED DESCRIPTION

Turning now to the drawing figures, and particularly FIG. 1, a buffer 10 for a human joint constructed in accordance with embodiments of the invention is illustrated. The buffer 10 is configured to be inserted into any human joint that is a bearing surface, such as the glenohumeral joint (shoulder joint) or the knee joint. Embodiments of the present invention will be discussed with respect to the knee joint, although it is to be understood that the invention is equally applicable to other joints.

The buffer 10 is configured to be inserted into a patient's knee in the space between the patient's femur and tibia and is intended to supplement any remaining articular cartilage 12 in the joint, or, in the instances where there is no remaining articular cartilage 12, provide a complete buffer between the femur and tibia. The buffer 10 is further sized so that it does not interfere with the menisci of the patient's knee, as illustrated in FIG. 1.

Figure 2:
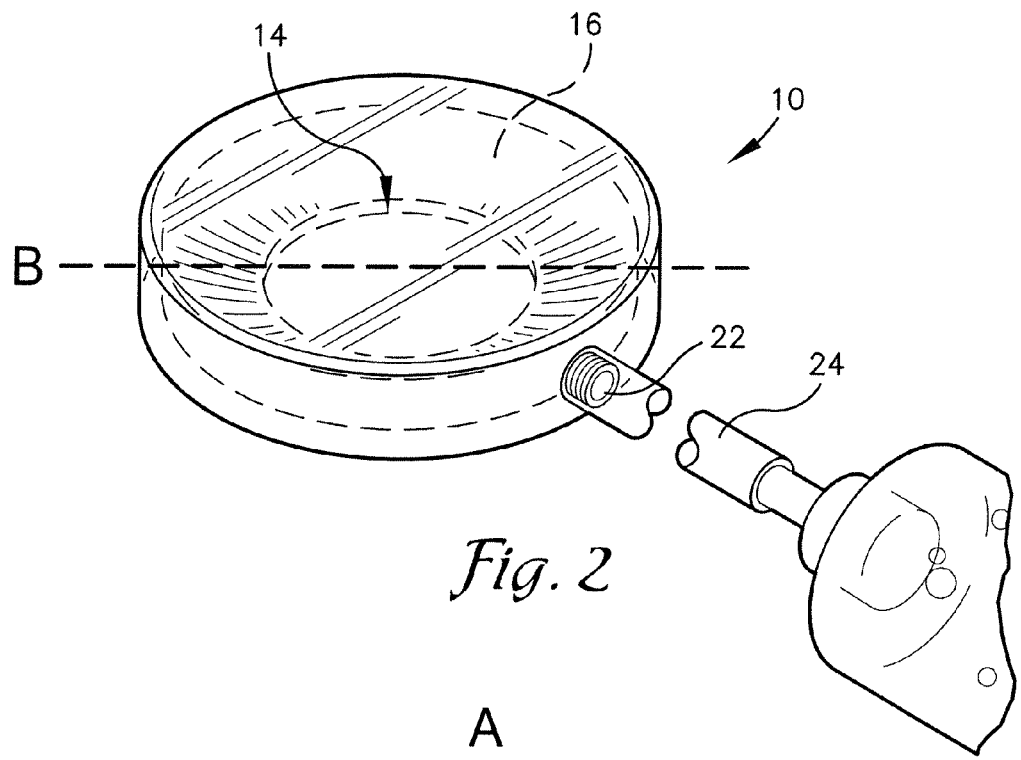
FIG. 2 is a perspective view of a buffer of the present invention comprising an outer sack and an inner ring.

The buffer 10 of an embodiment of the present invention comprises an outer sack 14 enclosing an inner ring 16 and further configured to receive a friction reducing fluid 18, as illustrated in FIGS. 1 and 2. As described in more detail below, the buffer 10 may be arthroscopically inserted into the patient's knee using a sleeve 20, illustrated in FIG. 4, especially designed for stable securement of the buffer 10 during the arthroscopic procedure.

The outer sack 14 of the buffer 10 is generally circular in shape, although the sack 14 may also be generally oval in shape while being inserted into the knee through the sleeve 20. The sack 14 is preferably approximately 10-50 mm in size, and more preferably approximately 30-60 mm, and most preferably approximately 35-45 mm. In an average patient, the space between the femur and tibia with an average amount of articular cartilage can be opened to 10-15 mm at arthroscopy but contract to 0 mm when the stress on the ligament is relaxed. The sack 14 having the inner ring 16 located therein has a height that is preferably at least the distance between the femur and tibia, i.e., approximately 10 mm, and is flexible. More preferably, the sack's height is slightly larger than the distance between the femur and tibia, such that the height of the sack 14 is approximately the same height as the inner ring. In embodiments of the invention, the buffer, including the inner ring, are manufactured in various sizes to accommodate differently-sized knee joints.

The sack 14 is preferably formed of a material that will be accepted by a human body and that is durable. Because of the pressure that the sack 14 will receive due to the contraction and movement of the femur and tibia, the sack 14 is further preferably formed of a pliable, resilient material. The material is also impermeable, such that the friction reducing fluid 18 does not escape from the sack 14. An exemplary material includes polyethylene, although any material having the above-described properties will suffice. The material forming the sack 14 may be translucent, as illustrated in FIG. 2, or opaque.

The sack 14 includes a one-way valve 22 that is fluidly connected to a hollow fluid line 24, as illustrated in FIGS. 1 and 2. The hollow fluid line 24 allows for passage of the fluid 18 therethrough. The friction reducing fluid 18, described in more detail below, is inserted into the sack 14 after the buffer 10 is positioned inside the patient's knee. The fluid 18 is inserted into the sack 14 via the fluid line 24, which will be of a length sufficiently long to allow insertion of the fluid 18 into the sack 14 via the sleeve 20 or other instrument, as also described in more detail below. The valve 22 preferably includes threads 23 (not shown) After the fluid 18 is inserted into the sack 14; the fluid line 24 is preferably unscrewed. Alternatively, the line 24 may be cut proximal to the sack 14 or otherwise formed so that it can be removed from the sack 14. The one-way valve 22 allows receipt of the friction reducing fluid 18 via the filler line 24 and after the buffer 10 is inserted into the patient's knee. The valve 22 is one-way, however, so that it does not allow for escape of the fluid 18 via the valve 22.

The friction reducing fluid 18 is any fluid that is accepted by a human body and that assists in allowing ease of movement of the inner ring 16 within the outer sack 14. Exemplary friction reducing fluids 18 include the patients own synovial fluid found in synovial joints, such as the knee joint, and artificial fluids, such as SYNVISC®, manufactured by Genzyme Corporation.

The inner ring 16 is generally circular in shape, although the ring 16 may also be generally oval in shape. During insertion, the inner ring is flexed to be oval in shape. The inner ring 16 is preferably approximately 20-60 mm in circumference, and more preferably approximately 25-55 mm, and most preferably approximately 27.5-32.5 mm. The inner ring 16 is manufactured therefore to fit within the sack 14. In preferred form, the inner ring 16 and sack 14 are manufactured as a unit, such that the inner ring 16 is located within the sack 14 and sold as single unit. As noted above, the sack and inner ring may be manufactured in various sizes to fit each particular patient.

The inner ring 16 is preferably solid and formed of a resiliently rigid material, such that the ring 16 can withstand, with little or no deformation along a longitudinal axis A, a relatively high degree of loading pressure occurring from placement between the femur and tibia, yet can also be flexed or otherwise deformed along a transverse axis B for ease of placement within the patient's knee. In particular, during insertion in the knee joint, the ring 16 can be compressed side to side along axis B for placement in the sleeve. However, the ring's 16 resiliently rigid material allows it to return to its generally circular shape once the pressure along the axis B is removed and the buffer is placed between the tibia and femur.

Figure 3:
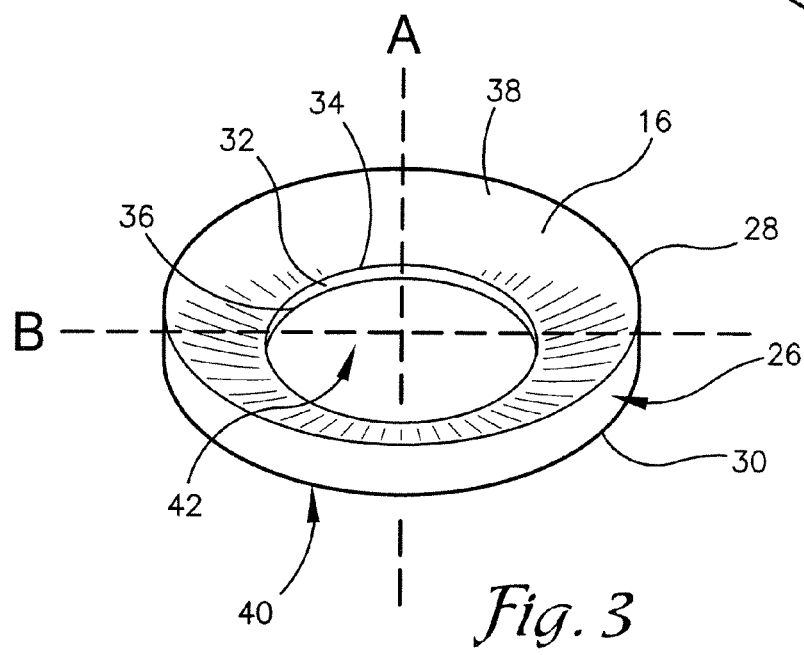
FIG. 3 is a perspective view of the inner ring of the buffer of the present invention.

The ring 16 preferably comprises an outer surface 26 having a top edge 28 and a bottom edge 30, an inner surface 32 having a top edge 34 and a bottom edge 36, a top surface 38, and a bottom surface 40. The outer, inner, top, and bottom surfaces 26,32,38,40 are preferably integrally formed and together define a hollow interior 42 of the ring 16. The top and bottom surfaces 38,40 are angled inwardly with respect to each other such that the top surface 38 extends downwardly from the top edge 28 of the outer surface 26 and to the top edge 34 of the inner surface 32, and similarly, the bottom surface 40 extends upwardly (not shown) from the bottom edge 30 of the outer surface 26 and up to the bottom edge 36 of the inner surface 32. In this manner, the top and bottom surfaces 38,40 form the ring 16 that is generally concave when viewed from a top of the ring 16 and flat when viewed from a bottom of the ring 16. This further provides a ring wherein a height of the ring along an outer diameter is larger than a height of the ring along an inner diameter, as illustrated in FIG. 3.

The concavity of the ring 16 and the orientation of the top and bottom surfaces 38,40 forms a generally V-shaped cross-section of the ring 16 when cut along the longitudinal axis A. The concavity assists with placement and retention of the buffer 10 between the patient's femur and tibia in the patient's knee. In particular, the buffer 10 is partially held in place within the patient's knee and between the femur and tibia by the load-bearing pressure that naturally occurs from the muscles, ligaments, and bones in the patient's knee and the weight of the body. However, to insure that the buffer 10 does not drift outside its proper placement when the knee is not exhibiting load-bearing pressure, the concave top and bottom surfaces 38, 40 of the inner ring 16 assist in locating the buffer 10 between the femur and tibia.

Figure 4:
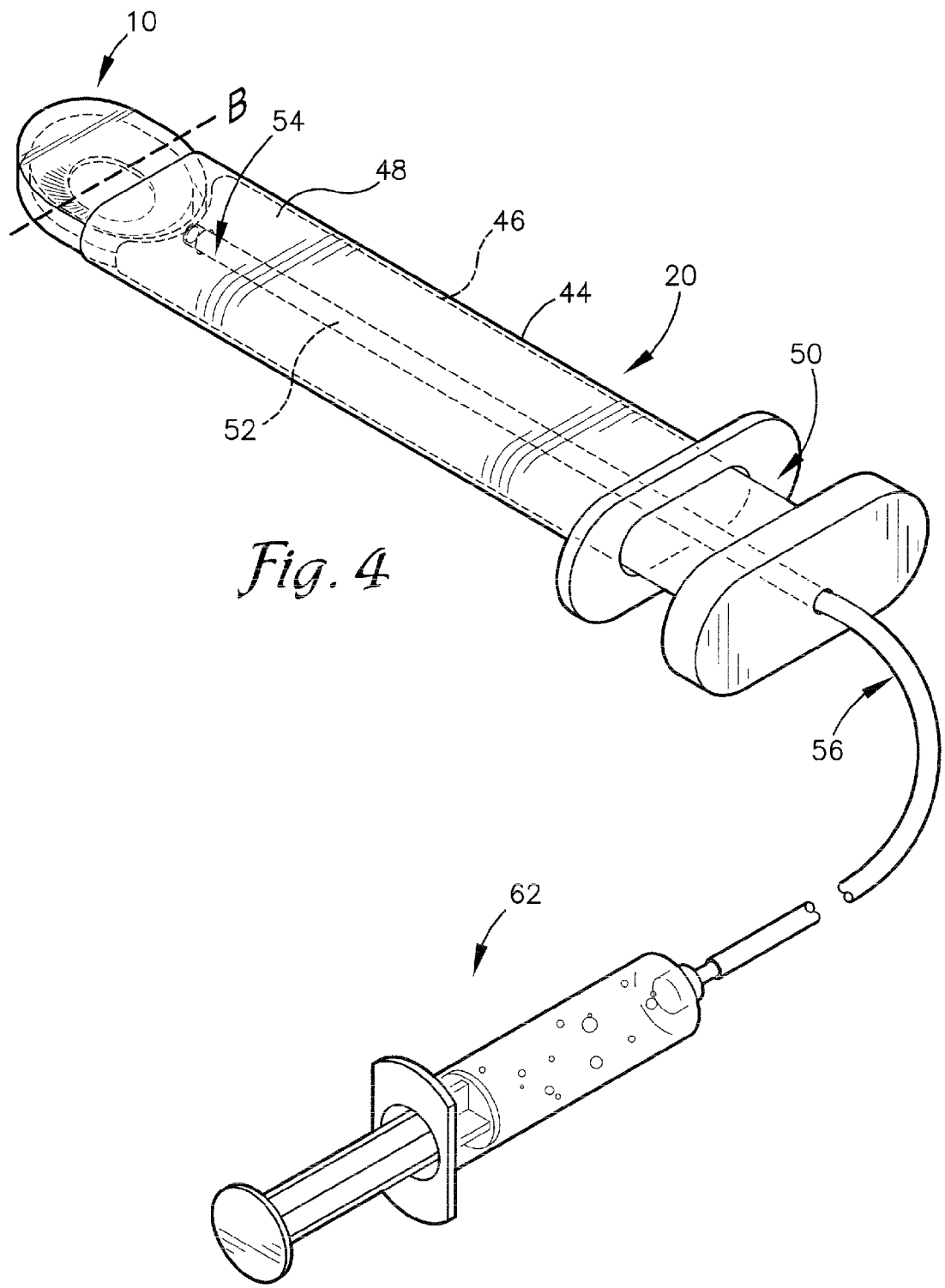
FIG. 4 is a perspective view of the buffer of the present invention received within a sleeve designed for arthroscopically inserting the buffer into a patient's knee.

As illustrated in FIG. 4, the sleeve 20 used to insert the buffer 10 into the knee comprises a generally ovoid, hollow body 44, a stylus or telescoping plunger 46 (not necessarily drawn to scale with respect to length in FIG. 4) having proximal and distal ends 48,50 and at least partially housed within the body 44, and the fluid line 24 having proximal and distal ends 54,56, partially housed within the body 44 and 46, and operable to allow the passage of fluid therethrough. The body 44 of the sleeve 20 is generally ovoid to accommodate the shape of the buffer 10 upon insertion, as described in more detail below. The fluid line 24 is passed through the plunger 46 and is screwed onto and fluidly connected with the valve 22 of the sack 14 at the proximal end 54 of the line 24 and with a fluid source (not shown) at the distal end 56 of the line 24.

The plunger 46 includes a curved neck 58 located at the proximal end 48 and operable to support the buffer 10 during placement in the patient's knee. The buffer 10 is preferably flexed along the transverse axis B into a generally ovoid shape so as to be partially inserted into the hollow body 44 of the sleeve 20, as illustrated in FIG. 4. The buffer 10 is inserted into the body 44 such that the valve 22 of the buffer 10 is screwed into fluid communication with the fluid line 24. Additionally, during insertion the buffer is supported by the curved neck 58 of the plunger 46.

The buffer 10 is preferably arthroscopically inserted into the patient's knee using the sleeve 20. The buffer 10 is flexed into the generally ovoid shape illustrated in FIG. 1 and then positioned within the sleeve 20. Flexing the buffer 10 into the ovoid shape facilitates insertion into the knee joint. The buffer 10 is held into place during insertion by being supported by the neck 58. Alternatively, the neck 58 could include further structure (not shown) for supporting and holding the buffer 10 at least partially in the sleeve 20 during insertion, such as a U-shaped arm that receives the buffer 10.

As discussed briefly above and as illustrated in FIG. 1, the buffer 10 is inserted between the tibia and femur of the knee joint. The buffer 10 can be inserted on either side of the knee, as illustrated in FIG. 1.

As noted above, upon insertion, the buffer 10 is flexed into the ovoid shape. Once the buffer 10 is released from the sleeve 20, it springs back into its generally circular shape, as illustrated in FIG. 1. Once inserted, the friction reducing fluid 18 is then inserted into the buffer 10 via the fluid line 24, which is fluidly connected between the one way valve 22 of the buffer 10 and the sleeve 20. Alternatively, the fluid 18 may be inserted into the buffer 10 prior to placement between the femur and tibia and/or prior to release from the sleeve 20. As noted above, after the fluid is inserted into the sack 14, the fluid line 24 is preferably physically separated from the buffer, so as to not be an irritant to the patient, by either cutting the line 24 proximal to the sack 14 or otherwise forming the line 24 so that it can be removed from the sack 14.

Once inserted, the rigidity of the inner ring 16 of the buffer 10 acts to keep the femur and tibia separated, such that the two bones are not contacting each other. Additionally, as noted above, once inserted, the load-bearing pressure of the femur and tibia assist in locating and holding the buffer in place between the bones. The concavity of the top and bottom surfaces 38, 40 of the ring 16 further assists in holding the buffer 10 in place, especially when there is no load-bearing pressure exhibited between the femur and tibia. The friction reducing fluid 18 then assists in movement of the femur and tibia against the buffer 10 and in particular, the inner ring 16 of the buffer 10.

The buffer 10 is advantageously independently held within the knee joint and does not have to be sutured to any muscle, ligament, or tendon. Moreover, the buffer 10 can be used with any amount of articular cartilage 12 and menisci, such that it is not limited to being only used with very little cartilage. Although the buffer of embodiments of the present invention are preferably permanent, it is to be understood that with time, the buffer 10 may become sufficiently worn so as to require replacement. However, such will likely not be the norm, and the buffer 10 is expected to last many years, depending on the activity level, weight, and age of the patient and other common degradation factors.

Although the invention has been described with reference to the preferred embodiment illustrated in the attached drawing figures, it is noted that equivalents may be employed and substitutions made herein without departing from the scope of the invention as recited in the claims. For example, the sleeve 20 could not include the fluid line 24, such that the friction reducing fluid 18 is inserted via a separate line and a syringe 62, as illustrated in FIG. 1.

Having thus described the preferred embodiment of the invention, what is claimed as new and desired to protected by Letters Patent includes the following:

1. An apparatus comprising:
   an outer sack;
   a generally circular or oval-shaped inner ring received within the outer sack, the inner ring having an outer surface having a top end and a bottom end, an inner surface having a top end and a bottom end, a top surface, and a bottom surface,
   wherein the top and bottom surfaces are angled inwardly with respect to each other, such that the top surface extends downwardly from the top end of the outer surface and to the top end of the inner surface, and the bottom surface extends upwardly from the bottom end of the outer surface and to the bottom end of the inner surface, such that the ring is generally concave; and
   a friction reducing fluid received within the outer sack,
   said apparatus configured for insertion between two bones of a human body so as to at least partially prevent the bones from contacting each other.

2. The apparatus of claim 1, wherein the apparatus is configured for insertion between a human's femur and tibia so as to at least partially prevent the femur and tibia from contacting each other.

3. The apparatus of claim 1, wherein the outer sack is generally circularly shaped.

4. The apparatus of claim 1, wherein the outer sack is formed of a pliable, resilient material.

5. The apparatus of claim 3, wherein the outer sack is formed of polyethylene.

6. The apparatus of claim 1, wherein the outer sack includes a one-way valve for receipt of the friction reducing fluid into the sack.

7. The apparatus of claim 1, wherein the inner ring is formed of a resiliently rigid material.

8. The buffer of claim 1, wherein the inner surface is smaller in height than the outer surface.

9. The buffer of claim 1, wherein the ring has a generally V-shaped cross section when cut along a plane orthogonal to the plane of the ring.

10. A buffer for placement between a human's femur and tibia, the buffer comprising:
    an outer sack formed of a pliable material and having a one-way valve;
    a generally circularly shaped inner ring received within the outer sack, the inner ring
      including
      a generally vertically-oriented outer surface along the circumference of the ring, said outer surface having a top end and a bottom end,
      a generally horizontally-oriented top surface extending downwardly from the top end of the outer surface, and
      a generally horizontally-oriented bottom surface extending upwardly from the bottom end of the outer surface,
      wherein the top surface and the bottom surface are angled inwardly with respect to each other, such that the ring is generally concave; and
    a friction reducing fluid received within the outer sack via the one-way valve,
    said apparatus configured for insertion between the femur and tibia so as to at least partially prevent the bones from contacting each other.

11. The buffer of claim 10, wherein the buffer is inserted between the femur and tibia using a sleeve.

12. The buffer of claim 11, wherein the sleeve comprises a generally ovoid, hollow body, a telescoping plunger having proximal and distal ends, and a fluid line having proximal and distal ends.

13. The buffer of claim 12, wherein the buffer flexes along a transverse axis for placement in the sleeve.

14. The apparatus of claim 10, wherein the ring further includes an inner surface positioned radially inward from the outer surface and coupled to the top surface and the bottom surface, the inner surface being smaller in height than the outer surface.

15. The apparatus of claim 10, wherein the ring has a generally V-shaped cross section when cut along a plane orthogonal to the plane of the ring.

* * * * *